(12) United States Patent
Yang et al.

(10) Patent No.: US 12,426,614 B2
(45) Date of Patent: Sep. 30, 2025

(54) LENTINULA EDODES-DERIVED SALTINESS ENHANCING PEPTIDE, METHOD FOR PREPARING THE SAME AND USE THEREOF

(71) Applicant: Shanghai Academy of Agricultural Sciences, Shanghai (CN)

(72) Inventors: Yan Yang, Shanghai (CN); Daoyou Chen, Shanghai (CN); Wanchao Chen, Shanghai (CN); Wen Li, Shanghai (CN); Peng Liu, Shanghai (CN); Di Wu, Shanghai (CN); Zhong Zhang, Shanghai (CN)

(73) Assignee: Shanghai Academy of Agricultural Sciences, Shanghai (CN)

( * ) Notice: Subject to any disclaimer, the term of this patent is extended or adjusted under 35 U.S.C. 154(b) by 0 days.

(21) Appl. No.: 18/912,396

(22) Filed: Oct. 10, 2024

(65) Prior Publication Data

US 2025/0143361 A1    May 8, 2025

(30) Foreign Application Priority Data

Nov. 7, 2023 (CN) .......................... 202311470960.X

(51) Int. Cl.
| | |
|---|---|
| *A23L 27/23* | (2016.01) |
| *A23L 27/00* | (2016.01) |
| *A23L 27/40* | (2016.01) |
| *C07K 1/34* | (2006.01) |
| *C07K 14/37* | (2006.01) |

(52) U.S. Cl.
CPC ............... *A23L 27/88* (2016.08); *A23L 27/45* (2016.08); *C07K 1/34* (2013.01); *C07K 14/37* (2013.01)

(58) Field of Classification Search
CPC .......... A23L 27/88; A23L 27/45; C07K 1/34; C07K 14/37
USPC ...................................................... 426/534
See application file for complete search history.

(56) References Cited

FOREIGN PATENT DOCUMENTS

| | | | | |
|---|---|---|---|---|
| CN | 102657328 A | * | 9/2012 | |
| CN | 108178781 A | * | 6/2018 | .............. A23L 27/11 |
| CN | 112725399 A | * | 4/2021 | .............. A61K 38/01 |

OTHER PUBLICATIONS

Translation of CN-102657328-A (Year: 2012).*
Translation of CN-108178781-A (Year: 2018).*
Translation of CN-112725399-A (Year: 2021).*

(Continued)

*Primary Examiner* — Brent T O'Hern
(74) *Attorney, Agent, or Firm* — Gavrilovich, Dodd & Lindsey LLP

(57) ABSTRACT

A *Lentinula edodes*-derived saltiness enhancing peptide, a method for preparing the same and use thereof are provided herein, belonging to the technical field of active peptides. The *Lentinula edodes*-derived saltiness enhancing peptide is derived from an enzymolysis extract of a *Lentinula edodes* fruiting body by flavourzyme and shows a strong ability to enhance saltiness. Compared with the saltiness value of a 4.0 g/L NaCl solution, the *Lentinula edodes*-derived saltiness enhancing peptide could replace about 50% of NaCl, thus reducing salt without reducing saltiness. Moreover, the *Lentinula edodes*-derived saltiness enhancing peptide also has a high umami value and can be used in preparation of low-salt foods including low-salt and flavor-enhancing foods.

10 Claims, 8 Drawing Sheets

Specification includes a Sequence Listing.

(56) References Cited

OTHER PUBLICATIONS

Mattar et al., A shiitake mushroom extract as a viable alternative to NaCl for a reduction in sodium in beef burgers: A sensory perspective, Abstract, British Food Journal. (Year: 2018).*

Tang et al., Purification of polysaccharide from Lentinus edodes water extract by membrane separation and its chemical composition and structure characterization (Year: 2020).*

* cited by examiner

LENTINULA EDODES-DERIVED SALTINESS ENHANCING PEPTIDE, METHOD FOR PREPARING THE SAME AND USE THEREOF

CROSS REFERENCE TO RELATED APPLICATION

This patent application claims the benefit and priority of Chinese Patent Application No. 202311470960.X, entitled "*LENTINULA EDODES*-DERIVED SALTINESS ENHANCING PEPTIDE, METHOD FOR PREPARING THE SAME AND USE THEREOF" filed with the China National Intellectual Property Administration on Nov. 7, 2023, the disclosure of which is incorporated by reference herein in its entirety as part of the present application.

REFERENCE TO SEQUENCE LISTING

A computer readable XML file entitled "GWP20240705451-sequence listing.xml" that was created on Oct. 10, 2024, with a file size of about 2,032 bytes, containing the sequence listing for this application, has been filed with this application, and is hereby incorporated by reference in its entirety.

TECHNICAL FIELD

The present disclosure belongs to the technical field of active peptides, and specifically relates to a *Lentinula edodes*-derived saltiness enhancing peptide, a method for preparing the same and use thereof.

BACKGROUND

Saltiness is one of the five basic tastes besides sour, sweet, bitter, and umami. Edible salt, as the most basic and widely used saltiness enhancer, can enrich the flavor and improve the quality of food. However, excessive salt intake may cause damage to organs such as the heart, brain, kidneys and so on, and increase the incidence of hypertension and the risk of depression. It is recommended by the World Health Organization (WHO) that a daily salt intake should not exceed 5 g, while the current average daily salt intake in China is 9 g to 11 g. Therefore, it has received widespread attention from countries around the world to find a way to "reducing salt without reducing saltiness", while the development of salt substitutes is particularly important. At present, the salt substitutes mainly include saltiness enhancing peptides and flavor improvers. Saltiness enhancing peptides extracted from natural plants and animals are regarded as a kind of ideal salt substitute.

Taste is produced by food acting on the tips of taste cells and ultimately feeding back from neuron to the brain. Saltiness can be sensed by many receptors or ion channels, including epithelial sodium channels (ENaCs), transient receptor potential vanilloid 1 (TRPV1), and transmembrane channel-like 4 (TMC4). Of them, the TMC4, a membrane protein with eight transmembrane domains, is a novel chloride ion channel that responds to high concentration of NaCl, and plays a vital role in the presentation of saltiness. At present, the taste characteristics of saltiness enhancing peptides need to be further explored.

*Lentinula edodes*, a main cultivated edible fungus in the world, is fresh in mouth feel, delicious in taste and rich in nutrients such as proteins, peptides, and amino acids. The *Lentinula edodes* is also a high-quality raw material for developing flavor products. Although the research system of edible fungus-derived umami peptides using molecular docking is relatively mature so far, there are relatively few studies on salty peptides and saltiness enhancing peptides at the molecular level. Moreover, there are currently no relevant cases of saltiness enhancing peptides prepared from the *Lentinula edodes*.

SUMMARY

A purpose of the present disclosure is to provide a *Lentinula edodes*-derived saltiness enhancing peptide. The *Lentinula edodes*-derived saltiness enhancing peptide has a desirable saltiness enhancing effect and may be used in the preparation of low-salt foods to achieve the technical effect of reducing salt without reducing saltiness, making the foods more green and healthy.

The present disclosure provides a *Lentinula edodes*-derived saltiness enhancing peptide, where the *Lentinula edodes*-derived saltiness enhancing peptide has an amino acid sequence set forth in SEQ ID NO: 1.

The present disclosure further provides a method for preparing the above *Lentinula edodes*-derived saltiness enhancing peptide, including the following steps: subjecting a *Lentinula edodes* fruiting body to first enzymolysis with a flavourzyme to obtain an enzymolysis extract by flavourzyme;
  subjecting the enzymolysis extract by flavourzyme to second enzymolysis with trypsin to obtain an enzymolysis extract by trypsin, and subjecting the enzymolysis extract by trypsin to solid-liquid separation to obtain an enzymolysis extract from *Lentinula edodes*;
  subjecting the enzymolysis extract from *Lentinula edodes* to ultrafiltration to obtain an ultrafiltration permeate, and subjecting the ultrafiltration permeate to nanofiltration to obtain a nanofiltration retentate, where the ultrafiltration is conducted at a molecular weight cut-off of 3 kDa, and the nanofiltration is conducted at a molecular weight cut-off of 200 Da; and
  subjecting the nanofiltration retentate to gel chromatography separation to obtain an eluate, and collecting the eluate of 100 min to 150 min, where the eluate includes the *Lentinula edodes*-derived saltiness enhancing peptide, and an eluent for the gel chromatography separation is water.

In some embodiments, the flavourzyme is added at 1,000 U/g into a dry product of the *Lentinula edodes* fruiting body.

In some embodiments, the first enzymolysis is conducted at 50° C. under a pH value of 7.0 for 45 min.

In some embodiments, the trypsin is added at 3,000 U/g into a dry product of the *Lentinula edodes* fruiting body.

In some embodiments, the second enzymolysis is conducted at 37° C. under a pH value of 8.0 for 45 min.

In some embodiments, the gel chromatography separation is conducted with a filler of Sephadex G-15 and a chromatographic column of XK16/100; and the eluent has a flow rate of 0.75 mL/min.

In some embodiments, the method further includes: subjecting the eluate to desalting purification, where a chromatographic column for the desalting purification is a Zip-Tip C18 microchromatographic column, and an eluent for the desalting purification is a 60 vol % acetonitrile aqueous solution containing 0.1 vol % trifluoroacetic acid (TFA).

In some embodiments, the first enzymolysis of the *Lentinula edodes* fruiting body with the flavourzyme specifically includes: mixing the flavourzyme, a dry product of the *Lentinula edodes* fruiting body, and water to allow enzymolysis; a mass-to-volume ratio of the dry product of the *Lentinula edodes* fruiting body to the water is 1 g: 30 mL.

The present disclosure further provides use of the *Lentinula edodes*-derived saltiness enhancing peptide described in the above technical solutions or a *Lentinula edodes*-derived saltiness enhancing peptide prepared by the preparation method described in the above technical solutions in a low-salt food.

Beneficial Effects

The present disclosure provides a *Lentinula edodes*-derived saltiness enhancing peptide, where the *Lentinula edodes*-derived saltiness enhancing peptide has an amino acid sequence set forth in SEQ ID NO: 1, specifically, DIQPEER. In the present disclosure, the *Lentinula edodes*-derived saltiness enhancing peptide is derived from an enzymolysis extract of a *Lentinula edodes* fruiting body and shows a highly strong ability to enhance saltiness. Compared with the saltiness value of a 4.0 g/L NaCl solution, the *Lentinula edodes*-derived saltiness enhancing peptide could replace about 50% of NaCl, thus reducing salt without reducing saltiness. Moreover, the *Lentinula edodes*-derived saltiness enhancing peptide also has a high umami value and may be used in preparation of low-salt foods including low-salt and flavor-enhancing foods.

BRIEF DESCRIPTION OF THE SEVERAL VIEWS OF THE DRAWINGS

To illustrate the examples of the present disclosure or the technical solutions in the prior art more clearly, the accompanying drawings required in the examples will be briefly introduced below.

DETAILED DESCRIPTION

Figure 1:
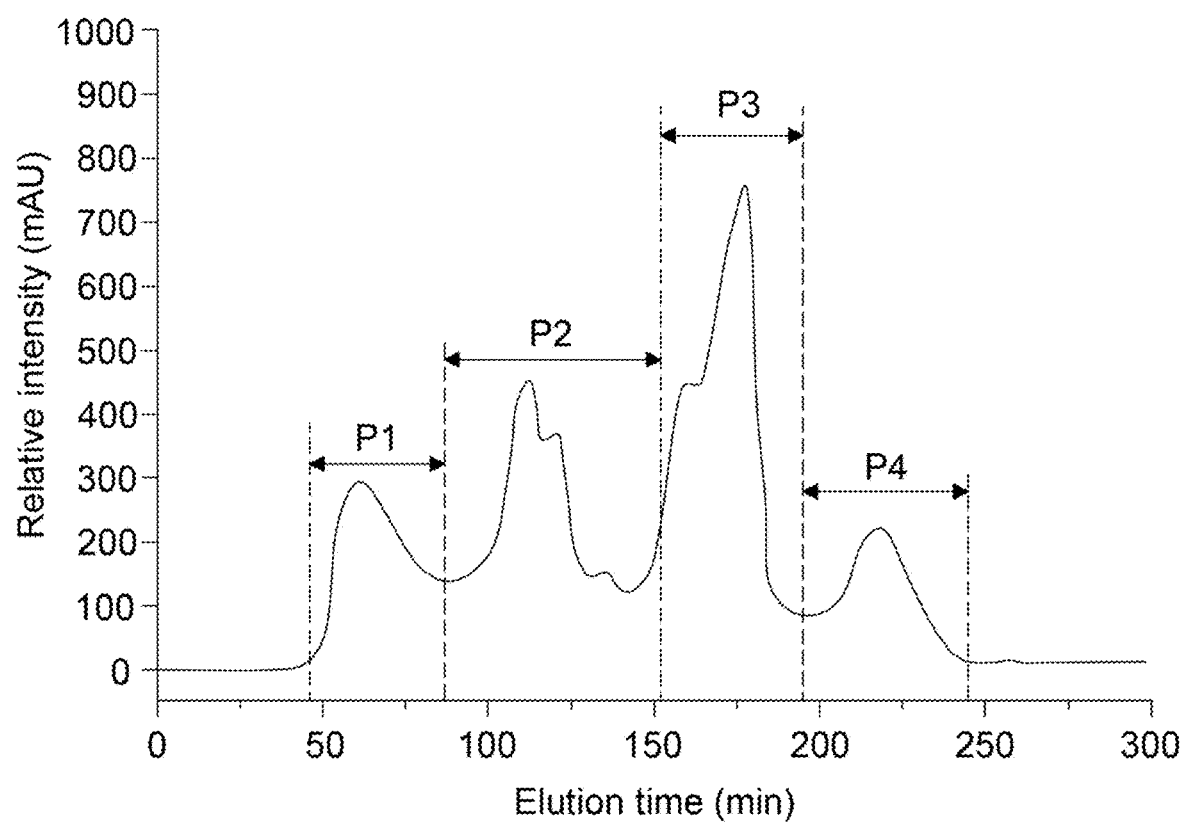
FIG. 1 shows a gel filtration chromatogram of the *Lentinula edodes* enzymolysis extract in Example 1.

The present disclosure provides a *Lentinula edodes*-derived saltiness enhancing peptide, where the *Lentinula edodes*-derived saltiness enhancing peptide has an amino acid sequence set forth in SEQ ID NO: 1.

In the present disclosure, the *Lentinula edodes*-derived saltiness enhancing peptide has a specific amino acid sequence of DIQPEER, a molecular weight of 885.4192 Da, a purity of not less than 98%, and a protein precursor of A0A1Q3E7W8. The *Lentinula edodes*-derived saltiness enhancing peptide has a significant saltiness enhancing effect and a high umami value.

The present disclosure further provides a method for preparing the *Lentinula edodes*-derived saltiness enhancing peptide, including the following steps: subjecting a *Lentinula edodes* fruiting body to first enzymolysis with a flavourzyme to obtain an enzymolysis extract by flavourzyme;

subjecting the enzymolysis extract by flavourzyme to second enzymolysis with trypsin to obtain an enzymolysis extract by trypsin, and subjecting the enzymolysis extract by trypsin to solid-liquid separation to obtain an enzymolysis extract from *Lentinula edodes*;

subjecting the enzymolysis extract from *Lentinula edodes* to ultrafiltration to obtain an ultrafiltration permeate, and subjecting the ultrafiltration permeate to nanofiltration to obtain a nanofiltration retentate, where the ultrafiltration is conducted at a molecular weight cut-off of 3 kDa, and the nanofiltration is conducted at a molecular weight cut-off of 200 Da; and subjecting the nanofiltration retentate to gel chromatography separation to obtain an eluate, and collecting the eluate of 100 min to 150 min, where the eluate includes the *Lentinula edodes*-derived saltiness enhancing peptide, and an eluent for the gel chromatography separation is water.

In the present disclosure, the *Lentinula edodes* fruiting body is preferably dried and crushed to obtain a *Lentinula edodes* powder. There is no particular limitation on the conditions for drying and crushing, and drying may be conducted using conventional methods in the art. The *Lentinula edodes* powder has a particle size preferably less than or equal to 80 mesh size.

In the present disclosure, the *Lentinula edodes* powder is preferably mixed with water to obtain a substrate for enzymolysis. A mass-to-volume ratio of the *Lentinula edodes* powder to the water is preferably 1 g: 30 mL.

In the present disclosure, the substrate is subjected to a first enzymolysis by flavourzyme to obtain the enzymolysis extract by flavourzyme. The flavourzyme is added at preferably 1,000 U/g to the *Lentinula edodes* powder; the first enzymolysis is conducted at preferably 50° C. under a pH value of preferably 7.0 for preferably 45 min.

In the present disclosure, after obtaining the enzymolysis extract by flavourzyme, the enzymolysis extract by flavourzyme is preferably subjected to enzyme inactivation. The enzyme inactivation is preferably conducted in a boiling water bath for preferably 10 min.

In the present disclosure, the enzymolysis extract by flavourzyme is preferably subjected to a second enzymolysis with trypsin to obtain an enzymolysis extract by trypsin. The trypsin is added at preferably 3,000 U/g to the *Lentinula edodes* powder. The second enzymolysis is conducted at preferably 37° C. under a pH value of preferably 8.0 for preferably 45 min.

In the present disclosure, the enzymolysis extract by trypsin is preferably subjected to enzyme inactivation; the enzyme inactivation has been defined and described in the above technical solution and will not be described in detail.

In the present disclosure, the enzymolysis extract by trypsin is preferably subjected to solid-liquid separation to obtain a supernatant, and the supernatant is collected to obtain an enzymolysis extract from *Lentinula edodes*. The solid-liquid separation is preferably conducted by centrifugation at preferably 4° C. under preferably 8,000 rpm for preferably 10 min.

In the present disclosure, the enzymolysis extract from *Lentinula edodes* is subjected to ultrafiltration to obtain an ultrafiltration permeate. The ultrafiltration is conducted at a molecular weight cut-off of 3 kDa and preferably a room temperature under a pressure difference (ΔP) of preferably 0.60 bar and a rotating velocity of preferably 250 rpm.

In the present disclosure, the ultrafiltration permeate is preferably subjected to nanofiltration to obtain a nanofiltration retentate. The nanofiltration is conducted at a molecular weight cut-off of preferably 200 Da.

In the present disclosure, the nanofiltration retentate is preferably subjected to concentration and freeze-drying to obtain a freeze-dried powder. In the present disclosure, a concentration factor is preferably 5 times, for example, 500 mL of the nanofiltration retentate is subjected to a rotary concentration preferably into 100 mL; the rotary concentration is conducted at preferably 50° C. to 60° C. There is no particular limitation on freeze-drying parameters, and conventional freeze-drying parameters in the art may be used.

In the present disclosure, the freeze-dried powder is preferably dissolved in distilled water to obtain a freeze-dried powder solution. Preferably, the freeze-dried powder solution has a concentration of 100 mg/mL.

In the present disclosure, the obtained freeze-dried powder solution is subjected to a gel chromatography separation to obtain an eluate, and the eluate of 100 min to 150 min is collected. Filler of the gel chromatography separation is preferably Sephadex G-15 and chromatographic column is preferably XK16/100. The eluent has a flow rate of preferably 0.75 mL/min.

In the present disclosure, the obtained eluate of 100 min to 150 min is preferably subjected to desalting purification, where a chromatographic column for the desalting purification is preferably a ZipTip C18 microchromatographic column, and an eluent for the desalting purification is preferably a 60 vol % acetonitrile aqueous solution containing 0.1 vol % TFA; and the eluent has a flow rate of preferably 0.5 mL/min.

In the present disclosure, the eluate of 100 min to 150 min is preferably subjected to UHPLC-Q-Orbitrap-MS/MS analysis to confirm that the *Lentinula edodes*-derived saltiness enhancing peptide has an amino acid sequence of DIQPEER. There is no particular limitation on a specific procedure of the UHPLC-Q-Orbitrap-MS/MS analysis and conventional identification procedures and parameters in the art may be used.

In the present disclosure, the *Lentinula edodes*-derived saltiness enhancing peptide is derived from an enzymolysis extract from a *Lentinula edodes* fruiting body and shows a strong ability to enhance saltiness. Compared with a 4.0 g/L NaCl solution, the *Lentinula edodes*-derived saltiness enhancing peptide can replace about 50% of NaCl, thus reaching reducing salt without reducing saltiness while showing a relatively desirable flavor-enhancing effect.

Based on this advantageous effect, the present disclosure further provides use of the *Lentinula edodes*-derived saltiness enhancing peptide or a *Lentinula edodes*-derived saltiness enhancing peptide prepared by the method in a low-salt food. The low-salt food preferably includes a low-salt and flavor-enhancing food.

In order to further illustrate the present disclosure, the technical solutions provided by the present disclosure are described in detail below in connection with accompanying drawings and examples, but these examples should not be understood as limiting the claimed scope of the present disclosure.

Example 1

A method for preparing a *Lentinula edodes*-derived saltiness enhancing peptide included the following steps:

1. Extraction of the *Lentinula edodes*-Derived Saltiness Enhancing Peptide

The *Lentinula edodes* fruiting body was dried, crushed, and sieved with an 80-mesh sieve to obtain a *Lentinula edodes* powder. The *Lentinula edodes* powder were mixed with distilled water in a mass-to-volume ratio of 1:30 g/mL, a flavourzyme was added, and enzymolysis was conducted at pH=7.0, 50° C. for 45 min (the flavourzyme was added at 1,000 U/g to the *Lentinula edodes* powder), and then the flavourzyme was inactivated in a boiling water bath for 10 min. The trypsin was added at 3,000 U/g *Lentinula edodes* powder therein, enzymolysis was conducted at pH=8.0 and 37° C. for 45 min, and then the trypsin was immediately heat-inactivated in boiling water for 10 min. A resulted mixture was centrifuged at 8,000 rpm for 10 min at 4° C. An enzymolysis extract from *Lentinula edodes* was collected, freeze-dried, and stored at −20° C.

2. Ultrafiltration and Nanofiltration

The enzymolysis extract from *Lentinula edodes* was subjected to ultrafiltration at a molecular weight cut-off of 3,000 Da, room temperature, ΔP=0.60 bar, and 250 rpm to obtain a filtrate. The filtrate was subjected to nanofiltration at a molecular weight cut-off of 200 Da (specifically, a resulting ultrafiltration permeate was loaded into two-thirds of a 200 Da dialysis bag, and then the dialysis bag containing the ultrafiltration permeate was placed in distilled water and dialyzed at room temperature). A resulting retentate, namely a substance with a molecular weight of less than 3,000 Da and greater than 200 Da, was collected, which was subjected to rotary concentration to 100 mL at 50° C. to 60° C., and then freeze-dried to obtain a freeze-dried powder.

3. Gel Chromatography

The freeze-dried powder obtained in step 2 was dissolved into a distilled water to prepare a sample of 100 mg/mL (the concentration may be adjusted according to the actual separation effect), and a sample volume after filtering the membrane was 2 mL. The filler was Sephadex G-15; the chromatographic column was XK16/100; the flow rate was 0.75 mL/min; and the detection wavelength was 220 nm. 4 fractions (P1 to P4) were collected within a retention time of 50 min to 250 min, as shown in FIG. 1, where the P1, P2, P3, and P4 were fractions with retention times of 50 min to 100 min, 100 min to 150 min, 150 min to 200 min, and 200 min to 250 min, respectively. The solutions in the collection tubes under the same spectral peak were combined, concentrated to a certain volume at 50° C. to 60° C., and freeze-dried.

4. The Sensory Evaluation and Peptide Content Determination were Conducted on the 4 Fractions Obtained in Step 3:

1) Sensory evaluation, specifically including: the sensory evaluation team consisted of 4 males and 6 females, aged 22 to 26 years old. All members of the team underwent sensory training and were able to accurately identify six basic taste characteristics. The standard taste solutions were 0.80 g/L citric acid, 10.00 g/L sucrose, 0.35 g/L quinine sulfate, 3.5 g/L sodium chloride, 3.5 g/L monosodium glutamate, and 0.85 g/L tannin, which were used to describe sour, sweet, bitter, salty, umami, and astringent, respectively. The sensory experiments were conducted at 25° C.±2° C. and 65% humidity.

The freeze-dried samples of the 4 fractions in step 3 were prepared into 1.0 mg/ml solutions separately, and a pH value of the sample solution was adjusted to 6.5 with either citric acid (1 mol/L) or sodium bicarbonate (1 mol/L). Panelists judged the taste characteristics of each sample and scored its saltiness intensity. NaCl solutions of different mass-to-volume ratios (0.1%, 0.20%, 0.30%, 0.40%, and 0.5%) were prepared, and the saltiness score of 0.30% NaCl solution was defined as 5 points, and the saltiness score increased or decreased by 1 point for every 0.1% increase or decrease in mass-to-volume ratio. The panelists recorded the intensity of the taste using a 10-point intensity scale (10 being the strongest taste and 0 being no taste). A total of 10 members in the team tasted the samples and scored them according to the above method to finally calculate an average value.

2) Peptide content determination: 0.1 g of the freeze-dried fraction was added into 1 mL of solution for extraction in the peptide content kit (Suzhou Michy Biomedical Technology Co., Ltd.), homogenized in an ice bath, then left for 30 min, centrifuged at 12,000 rpm, 4° C. for 10 min, and a resulted supernatant was collected. 10 µL of the supernatant sample was added to 190 µL of a working solution in the kit, incubated in a 60° C. oven for 30 min, and the absorbance of the mixed solution was measured at 562 nm in a 96-well plate. Peptide content (mg/g dry weight)=concentration of a standard×(measured absorbance of a sample-measured absorbance of blank control)÷(measured absorbance of the standard-measured absorbance of blank control)× V÷W; NOTE: the standard was a tetrapeptide standard with a concentration of 0.5 mg/mL; the blank control was water; V represented a volume of the collected supernatant, in mL; W represented a mass of the cubes/powder of *Lentinula edodes*, in g. The peptide content in the supernatant was further converted to its percentage of the dry weight of cubes/powder of *Lentinula edodes*.

The results of sensory evaluation and peptide content determination were shown in Table 1:

was dissolved in 0.1% formic acid solution, mixed thoroughly, and filtered by the membrane. An injection volume was 4 µL. The chromatographic column was ChromCore C18 (2.1 µm×100 mm, 1.9 µm), and the gradient elution was conducted at a flow rate of 0.3 mL/min. Mobile phase A was an aqueous solution containing 0.1% formic acid, and mobile phase B was a methanol solution containing 0.1% formic acid (gradient elution procedure: 0-1 min 10% mobile phase B; 1-20 min 100% mobile phase B; 20-22 min 100% B; 22-25 min 10% mobile phase B).

In the electron spray ionization (ESI) mode, mass spectrometric data fragment ion were collected in the mass range of (100-1,000) m/z. The ion source parameters were set as follows: capillary temperature 325° C., ion source spray voltage 4.5 kV, and capillary voltage 49 V. Data were collected using the Orbitrap mass spectrometer in full scan mode with a resolution of 70,000, a scan range of 200 to 2,000 by m/z, and a ddMS2 resolution of 17,500. The instrument was externally calibrated at the beginning of the analysis to confirm that the amino acid sequence in P2 was DIQPEER. The protein sequences of *L. edodes* were searched at NCBI. The identified peptide sequence was compared with the protein sequences of *L. edodes* to determine a protein precursor for the peptide.

6. The BIOPEP-UWM Sensory Peptide and Amino Acid Module Tool (https://biochemia.uwm.edu.pl/biopep-uwm/) was used to predict the taste characteristics of DIQPEER, and the molecular weight was found to be 885.4192 Da, the precursor protein was A0A1Q3E7W8, and its accession number in the NCBI database was LENED_005030. DIQPEER had the highest saltiness score and a relatively high umami score.

TABLE 1

Sensory evaluation and peptide content of fractions separated by gel filtration chromatography

| Fraction | Peptide content (mg/g) | Average saltiness value | Mouth feel feature |
|---|---|---|---|
| P1 | 563.29 ± 9.74[a] | 4.40 ± 0.76[b] | Slightly salty, slightly bitter, sour |
| P2 | 524.87 ± 8.13[b] | 6.80 ± 0.79[a] | Strong salty, slightly umami, slightly sweet |
| P3 | 260.85 ± 6.05[d] | 3.70 ± 0.95[c] | Sweet, slightly umami, slightly astringent |
| P4 | 376.16 ± 8.47[c] | 2.70 ± 0.67[d] | Bitter, slightly astringent |

NOTE:
different letters for the same index indicated significant difference ($P < 0.05$).

It was concluded from Table 1 that the differences in saltiness value of the 4 fractions were statistically significant ($p<0.05$). Fraction P2 scored the highest (6.80), which was slightly sweet and slightly umami. P1 had a saltiness value of 4.40 and tasted slightly salty, sour, and bitter. P3 and P4 had saltiness values of 3.70 and 2.70, respectively. P2 had a peptide content of 524.87 mg/g, such that P2 was selected for UHPLC-Q-Orbitrap-MS/MS analysis to determine its amino acid sequence.

5. UPLC-MS/MS Identification of Polypeptide Composition

The structure of fraction P2 obtained in step 3 was identified by UHPLC-Q-Orbitrap-MS/MS. The crude peptide fraction of P2 was desalted using a ZipTip C18 column with an elution program of 60% ACN/0.1% TFA. A collected sample solution was freeze-dried and used for subsequent sequence identification by mass spectrometry. The sample solution was analyzed using a Thermo Scientific Ultimate 3000 UPLC coupled to a Q Exactive Plus mass spectrometer (Q-Orbitrap MS/MS). The desalted sample 7. The amino acid sequence DIQPEER was synthesized by solid-phase synthesis (synthesized by GL Biochem (Shanghai) Co., Ltd. using polypeptide solid-phase synthesis, and desalted to obtain a peptide with a purity greater than 98%), and its saltiness was verified by sensory evaluation and threshold analysis. The sensory evaluation was by the method in step 4, and a concentration of the synthetic peptide solution prepared with distilled water was 1 mg/mL, specifically including: the sensory evaluation team consisted of 4 males and 6 females, aged 22 to 26 years old. All members of the team underwent sensory training and were able to accurately identify six basic taste characteristics. The standard taste solutions were 0.80 g/L citric acid, 10.00 g/L sucrose, 0.35 g/L quinine sulfate, 3.5 g/L sodium chloride, 3.5 g/L monosodium glutamate, and 0.85 g/L tannin, which were used to describe sour, sweet, bitter, salty, umami, and astringent, respectively. The sensory experiments were conducted at 25° C.±2° C. and 65% humidity. The panelists recorded the intensity of the taste using a 10-point intensity scale (10 being the strongest taste and 0 being no taste).

The threshold analysis was conducted by triangle test method. The synthetic peptide solution had an initial mass concentration of 1.0 mg/mL and was gradually diluted 1:1 (v:v) until the saltiness of the solution was no longer discernible. A mass concentration of the penultimate solution was recorded as the salinity threshold for the synthetic peptide.

Results were shown in Table 2.

TABLE 2

Sensory evaluation of synthetic peptide

| Synthetic peptide | Sour | Sweet | Bitter | Salty | Flavorful |
|---|---|---|---|---|---|
| DIQPEER | 1.90 ± 0.75 | 1.60 ± 0.49 | 2.10 ± 0.63 | 6.30 ± 0.64 | 4.30 ± 0.64 |

As shown in Table 2, the synthesized DIQPEER had different degrees of taste, with the saltiness value of 6.30 and the umami value of 4.30. The peptide also showed lower sourness (1.90), bitterness (2.10), and sweetness (1.60). DIQPEER has a saltiness threshold of 0.282 mM. In addition, the DIQPEER exhibited a stronger saltiness, and compared to the positive control group of NaCl (1.07 mM), the DIQPEER had a lower threshold.

Example 2

Molecular Docking of the *Lentinula edodes*-Derived Saltiness Enhancing Peptide

Figure 2:
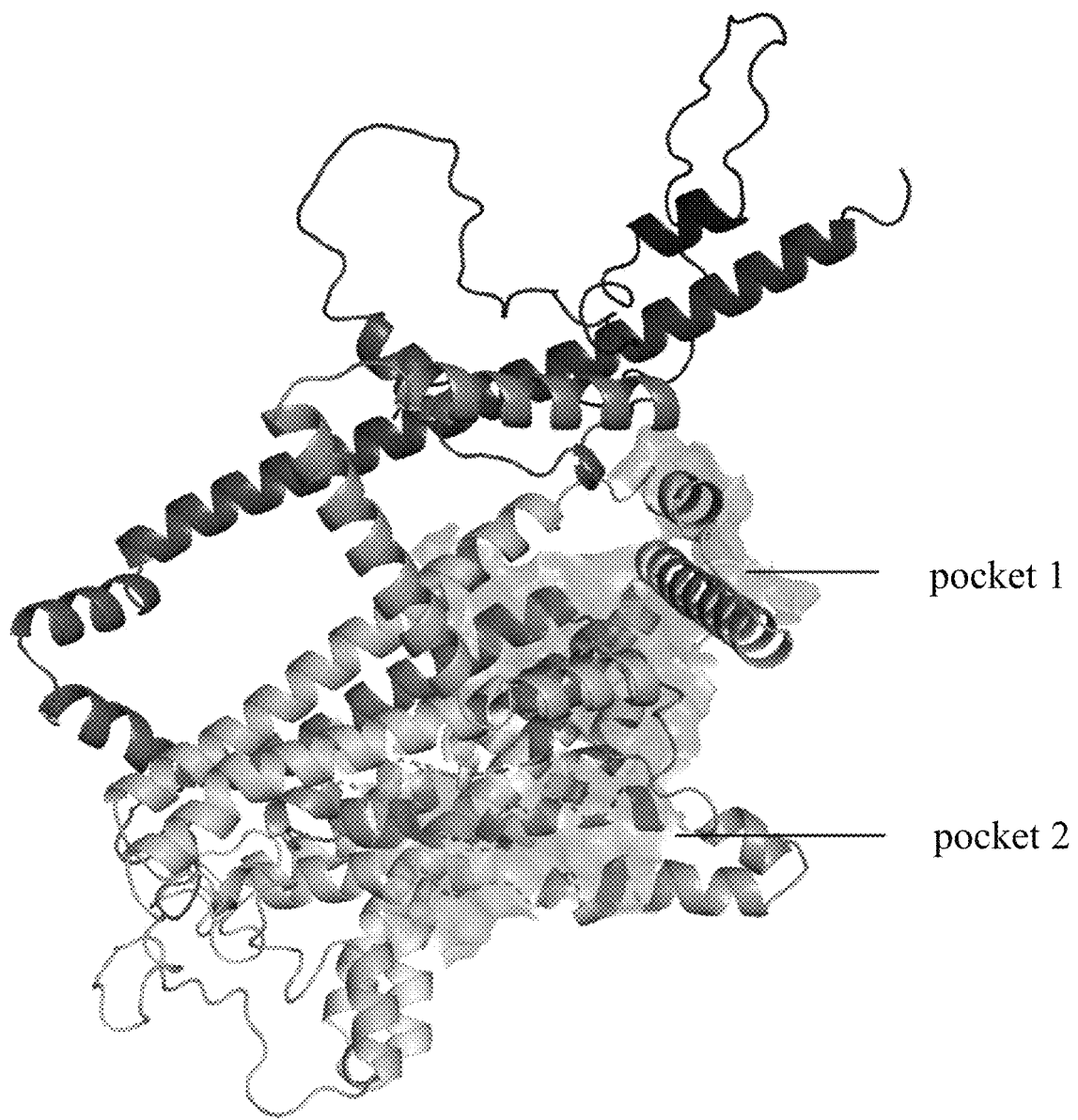
FIG. 2 shows a structure of the saltiness receptor TMC4 in Example 2 and binding pockets thereof.

In order to explore the binding mechanism of the *Lentinula edodes*-derived saltiness enhancing peptide in Example 1 to the TMC4 receptor, the molecular docking software Molecular Operating Environment (MOE) 2019 was used in this example to construct a three-dimensional structure of the saltiness enhancing peptide and minimize the energy thereof. The amino acid sequence of TMC4 receptor was retrieved from the NCBI database (https://www.ncbi.nlm.nih.gov/). A Swiss model online tool (https://swissmodel.expasy.org) was used to construct a 3D structure model of TMC4. The final constructed model of the saltiness receptor TMC4 was shown in FIG. 2.

Figure 3:
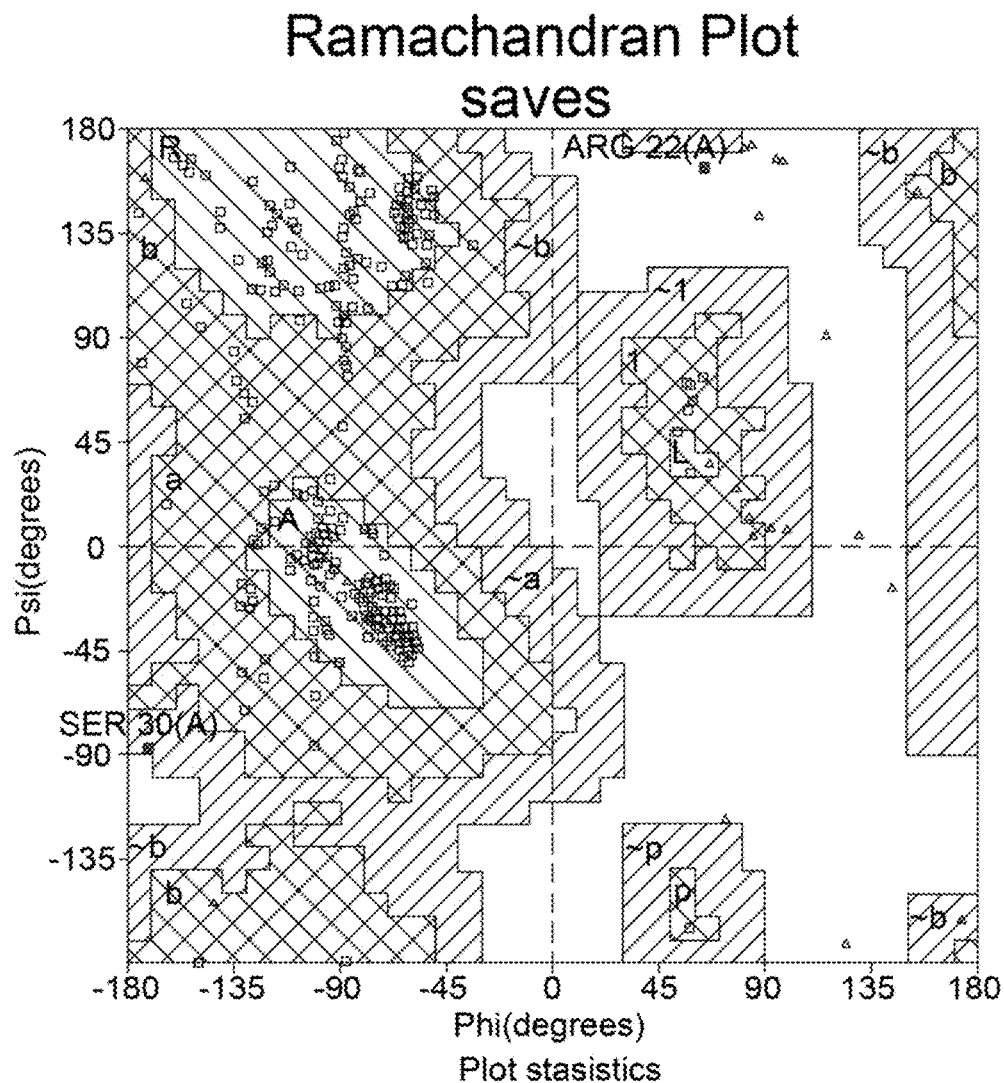
FIG. 3 shows Ramachandran plot evaluation of the saltiness receptor TMC4 in Example 2.

The structure of the receptor protein was evaluated using the Ramachandran plot (FIG. 3). 92.2% of the residues were in an optimal region of @ and Y angles, 7.4% of the residues were in other allowed regions, 0.2% of the residues were in the disallowed region, and 0.2% of the residues were in the prohibited region.

Figure 4:
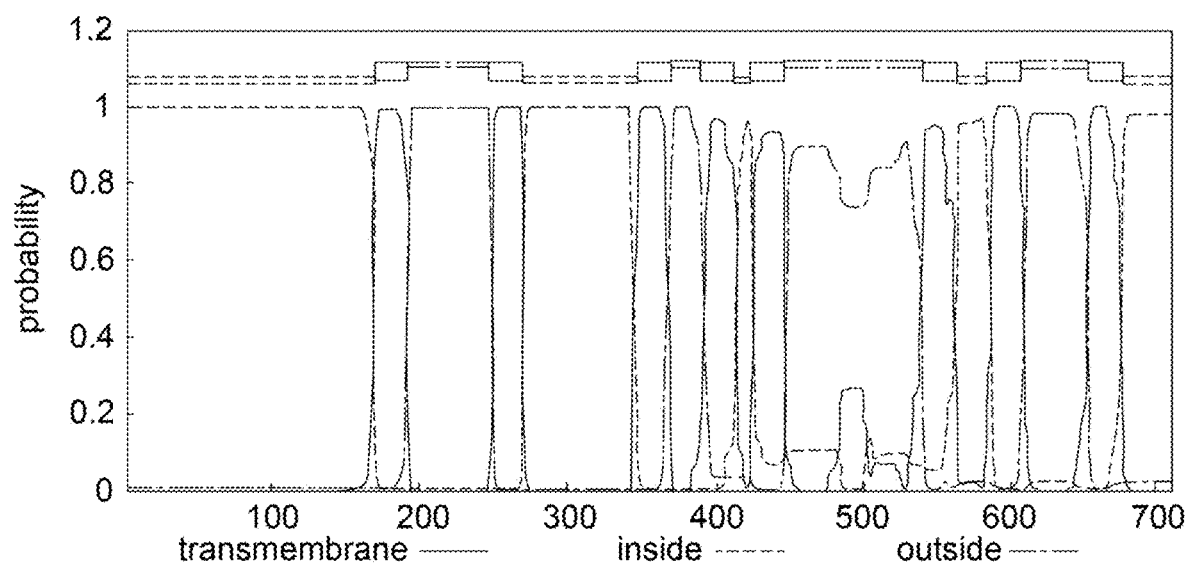
FIG. 4 is a diagram showing the transmembrane region of TMC4 predicted by TMHMM-2.0 server in Example 2.

A transmembrane region of TMC4 was predicted using the TMHMM-2.0 server (FIG. 4). The protein was found to have 8 transmembrane regions.

The DoGSiteScorer online tool was used to predict the allosteric pocket of TMC4 and classified according to the volume, surface, drugscore, and simplescore of the pocket to obtain 2 allosteric pockets of TMC4. The pocket 1 had a volume of Å3=2325.04, surface volume Å2=2783.62, drugscore=0.83, simplescore=0.66. The pocket 2 had a volume of Å3=957.57, surface volume Å2-818.24, drugscore=0.83, simplescore=0.59. The predicted amino acid binding sites of pocket 1 and pocket 2 of the TMC4 receptor were shown in Table 3. Therefore, the saltiness enhancing peptide was subjected to molecular docking with the binding pockets, pocket 1 and pocket 2 separately.

TABLE 3

Amino acid binding sites of saltiness receptor TMC4

| Amino acid binding site of pocket 1 in TMC4 | | | Amino acid binding site of pocket 2 in TMC4 | |
|---|---|---|---|---|
| Gln155 | Arg314 | Glu525 | Tyr163 | Phe526 |
| Phe156 | Ile315 | Phe526 | Ser397 | Gln527 |
| Gly157 | Tyr318 | Gln527 | Ile400 | Asp530 |
| Ala158 | Glu319 | Val528 | Ala401 | Glu531 |
| Gly159 | Lys321 | Pro529 | Asn404 | Leu533 |
| Thr160 | Val322 | Asp530 | Phe405 | Gly534 |
| Glu161 | Glu323 | Val532 | Pro408 | Leu535 |
| Ser162 | Glu325 | Leu571 | Pro409 | Tyr537 |
| Tyr163 | Glu326 | Cys575 | Lys412 | Ala538 |
| Ser165 | Thr327 | Ser576 | Arg437 | Val541 |
| Leu166 | Arg330 | Pro577 | Leu487 | Val542 |
| Arg272 | Pro408 | Ala578 | Leu488 | Lys559 |
| Ser275 | Phe411 | Ala579 | Phe490 | Phe560 |
| Gly276 | Lys412 | Arg580 | Asp491 | Leu563 |
| Gln279 | Pro416 | Thr581 | Leu492 | Lys567 |
| Ala287 | Arg422 | Phe582 | Thr494 | Thr570 |
| Ser290 | Ser423 | Arg583 | Val495 | Leu571 |
| Tyr291 | Gln425 | Ala584 | Val498 | Cys575 |
| Arg294 | Ile426 | Ser585 | Gln503 | Arg580 |
| Leu303 | Val427 | Ala586 | Arg506 | Thr581 |
| His308 | Ile429 | Ala587 | Leu520 | Phe582 |
| Leu311 | Leu430 | Asn588 | Gln524 | |
| Arg312 | Thr433 | Phe590 | Glu525 | |

According to the docking results, DIQPEER could respectively enter the two binding pockets (pocket 1 and pocket 2) of TMC4. DIQPEER had a docking energy of −10.9988 kcal/mol to pocket 1 of TMC4 and a docking energy of −10.3088 kcal/mol to pocket 2 (Table 4).

TABLE 4

Molecular docking energy and threshold analysis of DIQPEER

| Synthetic peptide | Length | Molecular weight | Threshold (mmol/L) | Docking energy (kcal/mol) pocket 1 | Docking energy (kcal/mol) pocket 2 | Precursor protein |
|---|---|---|---|---|---|---|
| DIQPEER | 7 | 885.4192 | 0.282 | −10.9988 | −10.3088 | A0A1Q3E7W8 |

Figure 5:
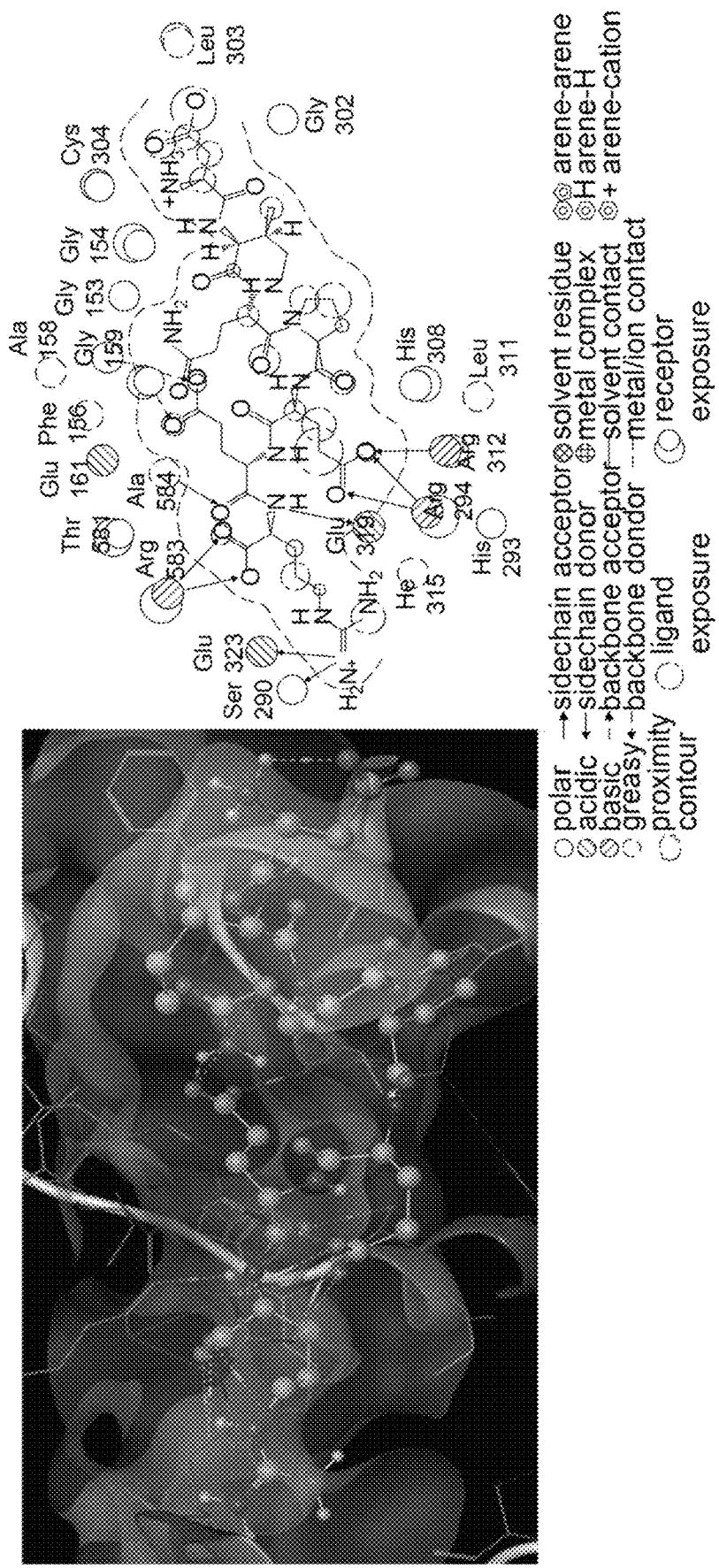
FIG. 5 is an image showing 2D and 3D view of the interaction between DIQPEER and pocket 1 of TMC4 in Example 2.
Figure 6:
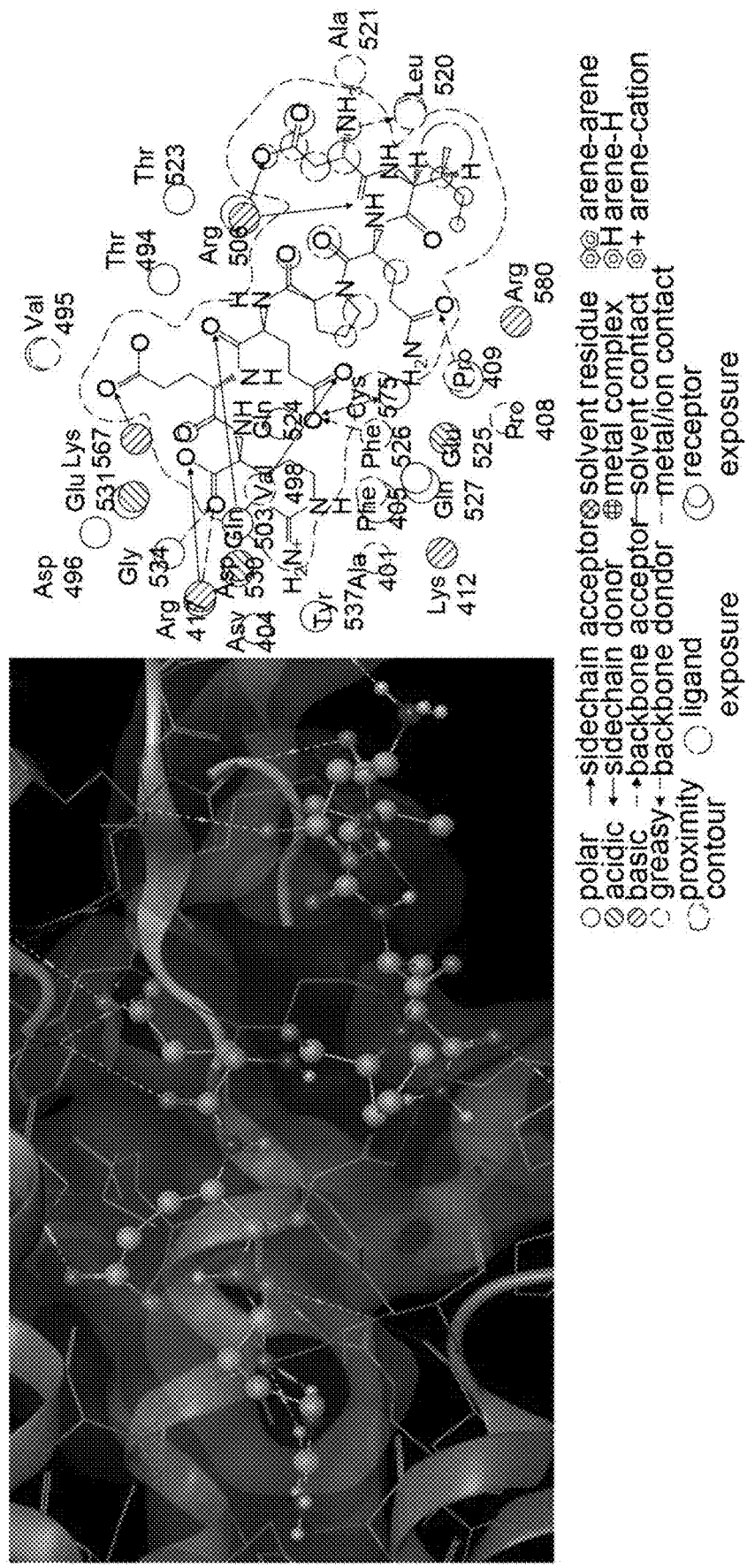
FIG. 6 is an image showing 2D and 3D view of the interaction between DIQPEER and pocket 2 of TMC4 in Example 2.

Hydrogen bonding and electrostatic interactions are the main ways in which DIQPEER interacts with TMC4 receptors. DIQPEER interacts with TMC4 pocket 1 (FIG. 5) and could form hydrogen bonds with multiple binding sites (Glu319, Ser290, Glu323, Arg294, Arg312, Ala584, Gly157, Gly159, and Arg583). Glu323, Arg312, Arg294, and Arg583 formed ionic bonds with the ligand DIQPEER. DIQPEER interacted with TMC4 pocket 2, as shown in FIG. 6, Leu520, Cys575, Arg506, Pro409, Gln503, Phe526, Lys567, Gly534, and Arg437 in TMC4 pocket 2 formed hydrogen bonds with Q3, E5, E6, and R7 in the DIQPEER ligand. Arg294, Arg312, Arg583, and Glu323 in pocket 2 formed ionic interactions with the ligand.

The above results could further verify the sensory evaluation result that DIQPEER tasted salty. The stable binding of DIQPEER and TMC4 indicated that DIQPEER was likely to activate the saltiness receptor of TMC4 protein and bind to same, thereby perceiving the saltiness. Moreover, hydrogen bonding interactions and ionic interactions played a key role in enhancing the saltiness.

Example 3

Saltiness Enhancing Effect of DIQPEER

Figure 7:
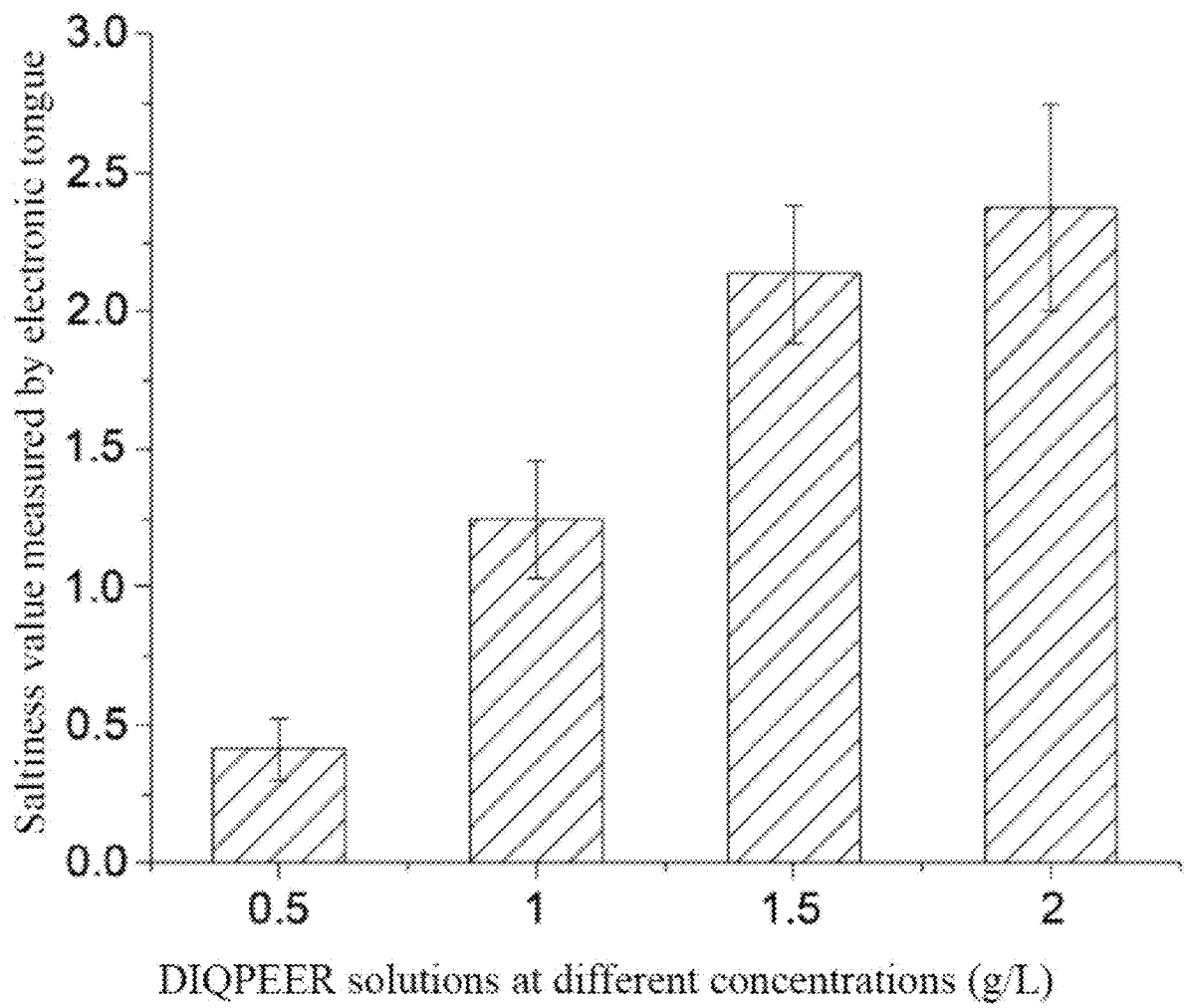
FIG. 7 shows saltiness value measured by electronic tongue of DIQPEER solutions of different concentrations in Example 3.

In order to understand the flavor characteristics of DIQPEER synthetic peptide solutions of different concentrations in NaCl solutions of different concentrations, 0.5 g/L, 1.0 g/L, 1.5 g/L, and 2.0 g/L DIQPEER synthetic peptide aqueous solutions were added into 3.5 g/L, 3.0 g/L, 2.5 g/L, and 2.0 g/L NaCl solutions, respectively, for electronic tongue measurement. The results were shown in FIG. 7. As shown in FIG. 7, DIQPEER synthetic peptide aqueous solutions of different concentrations exhibited different degrees of saltiness, and the saltiness intensity increased with the increase of the concentration.

Figure 8:
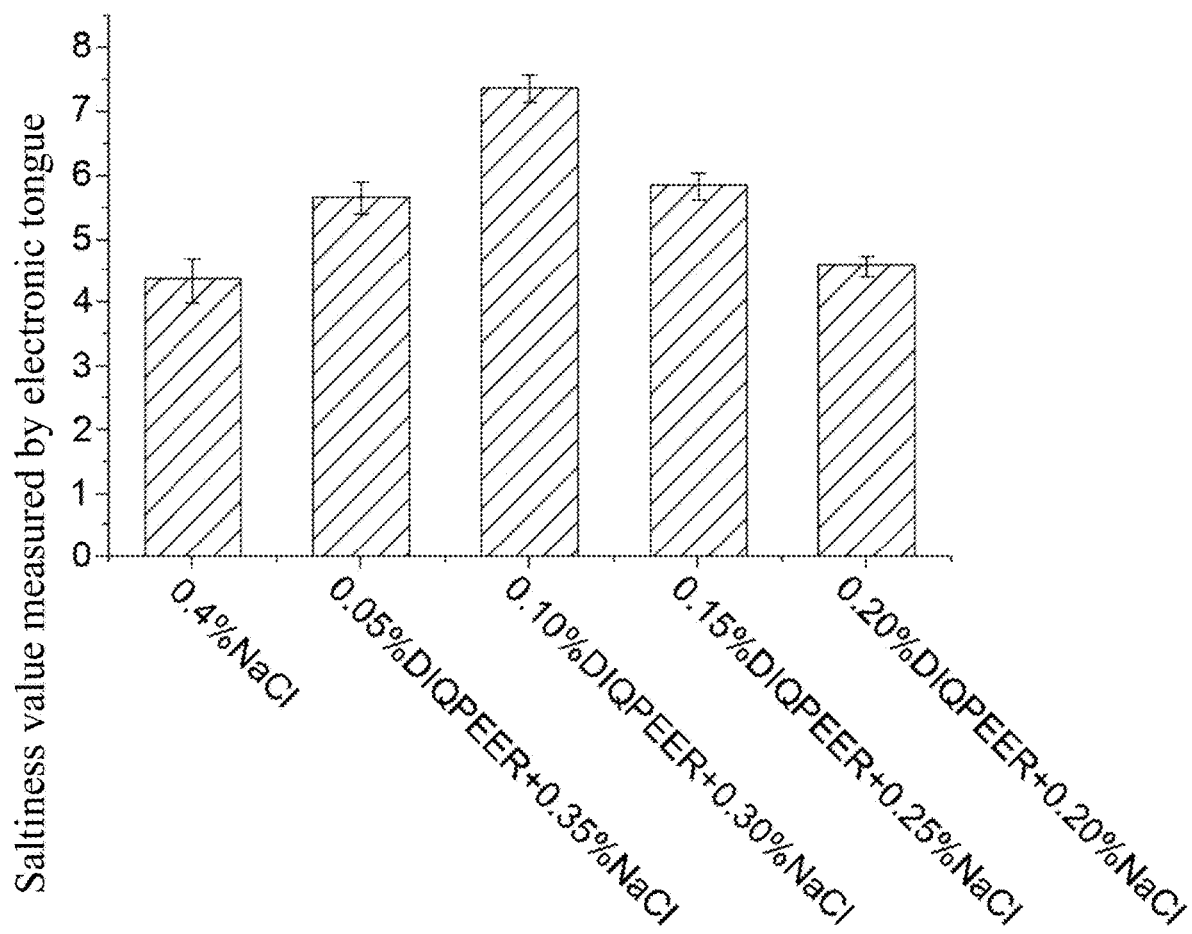
FIG. 8 shows saltiness value measured by electronic tongue reflecting synergistic salinity enhancement effects of DIQPEER solutions of different concentrations and NaCl solutions of different concentrations in Example 3.

The synergistic effect of DIQPEER and NaCl solution was shown in FIG. 8. As shown in FIG. 8, as the concentration of the synthetic peptide increased, DIQPEER exhibited different degrees of saltiness enhancement, and the saltiness enhancement curve showed a trend of increasing and then decreasing. When 1.0 g/L synthetic peptide was added to 3.0 g/L NaCl solution, the salinity of the solution increased significantly. Compared with the saltiness value of 4.0 g/L NaCl solution, DIQPEER had the strongest saltiness enhancement ability, which increased by 69.59%. As the concentration of synthetic peptides increased, the concentration of NaCl solution decreased and the saltiness enhancing effect weakened. Without affecting the overall solution taste, DIQPEER could replace about 50% of NaCl compared to the saltiness value of 4.0 g/L NaCl solution. In general, DIQPEER and NaCl solutions had a synergistic effect, which enhanced the saltiness of the solution and thus reducing salt without reducing saltiness.

It can be concluded from the above examples that the present disclosure provides a novel *Lentinula edodes*-derived saltiness enhancing peptide DIQPEER, and the *Lentinula edodes*-derived saltiness enhancing peptide has a strong saltiness enhancing effect and a strong umami value.

Although the above example has described the present disclosure in detail, it is only a part of, not all of, the examples of the present disclosure. Other examples may also be obtained by persons based on the examples without creative efforts, and all of these examples shall fall within the protection scope of the present disclosure.

subjecting a *Lentinula edodes* fruiting body to a first enzymolysis with a flavourzyme to obtain an enzymolysis extract by flavourzyme;

subjecting the enzymolysis extract by flavourzyme to a second enzymolysis with a trypsin to obtain an enzymolysis extract by trypsin, and subjecting the enzymolysis extract by trypsin to solid-liquid separation to obtain an enzymolysis extract from *Lentinula edodes;* subjecting the enzymolysis extract from *Lentinula edodes* to ultrafiltration to obtain an ultrafiltration permeate, and subjecting the ultrafiltration permeate to nanofiltration to obtain a nanofiltration retentate, wherein the ultrafiltration is conducted at a molecular weight cut-off of 3 kDa, and the nanofiltration is conducted at a molecular weight cut-off of 200 Da; and subjecting the nanofiltration retentate to gel chromatography separation to obtain an eluate, and collecting the eluate of 100 min to 150 min, wherein the eluate comprises the *Lentinula edodes*-derived saltiness enhancing peptide, and an eluent for the gel chromatography separation is water.

2. The method according to claim 1, wherein the flavourzyme is added at 1,000 U/g to a dry product of the *Lentinula edodes* fruiting body.

3. The method according to claim 1, wherein the first enzymolysis is conducted at 50° C. under a pH value of 7.0 for 45 min.

4. The method according to claim 3, wherein the flavourzyme is added at 1,000 U/g to a dry product of the *Lentinula edodes* fruiting body.

5. The method according to claim 1, wherein the trypsin is added at 3,000 U/g to a dry product of the *Lentinula edodes* fruiting body.

6. The method according to claim 5, wherein the flavourzyme is added at 1,000 U/g to a dry product of the *Lentinula edodes* fruiting body.

7. The method according to claim 5, wherein the second enzymolysis is conducted at 37° C. under a pH value of 8.0 for 45 min.

8. The method according to claim 1, wherein the gel chromatography separation is conducted with a filler of Sephadex G-15 and a chromatographic column of XK16/100; and the eluent has a flow rate of 0.75 mL/min.

9. The method according to claim 1, further comprising: subjecting the eluate to desalting purification, wherein a chromatographic column for the desalting purification is a ZipTip C18 microchromatographic column, and an eluent

SEQUENCE LISTING

```
Sequence total quantity: 1
SEQ ID NO: 1            moltype = AA   length = 7
FEATURE                 Location/Qualifiers
source                  1..7
                        mol_type = protein
                        organism = synthetic construct
SEQUENCE: 1
DIQPEER                                                              7
```

What is claimed is:

1. A method for preparing a *Lentinula edodes*-derived saltiness enhancing peptide having an amino acid sequence set forth in SEQ ID NO: 1, comprising the following steps:

for the desalting purification is a 60 vol % acetonitrile aqueous solution containing 0.1 vol % trifluoroacetic acid (TFA).

10. The method according to claim 9, wherein the first enzymolysis of the *Lentinula edodes* fruiting body by the flavourzyme specifically comprises: mixing the flavourzyme, a dry product of the *Lentinula edodes* fruiting body and water to allow enzymolysis; wherein a mass-to-volume ratio of the dry product of the *Lentinula edodes* fruiting body to the water is 1 g:30 mL.

* * * * *